(12) United States Patent
Handley et al.

(10) Patent No.: US 10,500,145 B2
(45) Date of Patent: Dec. 10, 2019

(54) BODY INK COMPOSITIONS AND APPLICATORS

(71) Applicant: inkbox ink Inc., Toronto (CA)

(72) Inventors: Tyler James Handley, Toronto (CA); Braden Handley, Toronto (CA); Christopher Blain Caputo, Toronto (CA); Adam Manuel Zrehen, Toronto (CA)

(73) Assignee: inkbox ink inc., Toronto, ON ( * ) Notice: Subject to any disclaimer, the term of this patent is extended or adjusted under 35 U.S.C. 154(b) by 236 days.

(21) Appl. No.: 15/179,121

(22) Filed: Jun. 10, 2016

(65) Prior Publication Data

US 2016/0367460 A1  Dec. 22, 2016

Related U.S. Application Data

(60) Provisional application No. 62/181,918, filed on Jun. 19, 2015.

(51) Int. Cl.
*A61K 8/49* (2006.01)
*A61Q 1/02* (2006.01)
(Continued)

(52) U.S. Cl.
CPC ............. *A61K 8/498* (2013.01); *A61K 8/24* (2013.01); *A61K 8/34* (2013.01); *A61K 8/345* (2013.01); *A61K 8/73* (2013.01); *A61K 8/922* (2013.01); *A61K 8/97* (2013.01); *A61Q 1/02* (2013.01); *A61Q 1/025* (2013.01); *B32B 7/12* (2013.01); *C09D 11/00* (2013.01); *D06M 11/58* (2013.01); *A61K 2800/43* (2013.01); *A61K 2800/48* (2013.01); *A61K 2800/87* (2013.01); *B32B 2405/00* (2013.01)

(58) Field of Classification Search
CPC ...... A61K 2800/43; A61Q 1/025; A61Q 1/02; A61Q 5/10
See application file for complete search history.

(56) References Cited

U.S. PATENT DOCUMENTS 4,594,276 A  6/1986 Relyea
6,074,721 A  6/2000 Moore
(Continued)

FOREIGN PATENT DOCUMENTS

CN  101781530  7/2010
EP  0251063   1/1988
(Continued)

OTHER PUBLICATIONS

Djerassi et al. "Naturally Occurring Oxygen Heterocyclics. IX. Isolation and Characterization of Genipin", Journal of Organic Chemistry, Dec. 1960, vol. 25, issue 12, pp. 2174-2177.
(Continued)

*Primary Examiner* — Kortney L Klinkel
(74) *Attorney, Agent, or Firm* — Fish & Richardson P.C.

(57) ABSTRACT

A temporary tattooing ink is produced from concentrated genipin. In one embodiment, the concentrated genipin forms part of a solution. In another embodiment, the genipin is provided in a gel form which also includes a solvent and a thickening agent. Finally, an applicator is described into which genipin may be embedded for applying to a user's skin.

11 Claims, 6 Drawing Sheets

(51) Int. Cl.
  *A61K 8/97*   (2017.01)
  *A61K 8/24*   (2006.01)
  *A61K 8/34*   (2006.01)
  *A61K 8/73*   (2006.01)
  *A61K 8/92*   (2006.01)
  *C09D 11/00*  (2014.01)
  *B32B 7/12*   (2006.01)
  *D06M 11/58*  (2006.01)

(56) References Cited

U.S. PATENT DOCUMENTS

| | | | |
|---|---|---|---|
| 6,106,852 | A | 8/2000 | Vineberg |
| 2005/0234322 | A1 | 10/2005 | Lober |
| 2006/0068146 | A1 | 3/2006 | Marks |
| 2008/0260668 | A1 | 10/2008 | Vidalenc |
| 2009/0120565 | A1 | 5/2009 | Marshall |
| 2010/0196298 | A1 | 8/2010 | Andre |
| 2012/0244316 | A1 | 9/2012 | Dobler |
| 2013/0225669 | A1* | 8/2013 | Reich ............... A01N 1/0231 514/456 |
| 2014/0188074 | A1 | 7/2014 | Jacques |
| 2014/0350127 | A1 | 11/2014 | Cano |
| 2015/0209258 | A1* | 7/2015 | Gebert-Schwarzwalder ............... A61K 8/4953 8/423 |

FOREIGN PATENT DOCUMENTS

| | | |
|---|---|---|
| JP | 2000309740 | 11/2000 |
| TW | 200908991 | 3/2009 |
| WO | 2013045701 | 4/2013 |
| WO | WO 2013/070682 | 5/2013 |

OTHER PUBLICATIONS

Frick D., "The coloration of food", Review of Progress in Coloration and Related Topics, 2003, vol. 33, issue 1, pp. 15-32. doi:10.1111/j.1478-4408.2003.tb00141.x.

Morel et al. "Current Trends in the Chemistry of Permanent Hair Dyeing", Chemical Reviews, 2011, vol. 111 issue 4, pp. 2537-2561. doi:10.1021/cr1000145.

Di Tommaso et al. "From iridoids to dyes: a theoretical study on genipin reactivity", RSC Advances, 2014, vol. 4, Issue 22, pp. 11029-11038. doi:10.1039/C3RA47159D.

Mi et al. "Characterization of ring-opening polymerization of genipin and pH-dependent cross-linking reactions between chitosan and genipin", Journal of Polymer Chemistry: Part A Polymer Chemistry, 2005, vol. 43, issue 10, pp. 1985-2000. doi:10.1002/pola.20669.

Park et al. "Isolation and Characterization of Water-Soluble Intermediates of Blue Pigments Transformed from Genipiside of Garenia jasminoides", Journal of Agriculture and Food Chemistry, 2002, vol. 50, issue 22, pp. 6511-6514. doi:10.1021/jf020499b.

Fujikawa S et al. "Brilliant skyblue pigment formation from gardenia fruits", Journal of Fermentation Technology, Jan. 1987, vol. 65, issue 4, pp. 419-424. doi:10.1016/0385-6380(87)90138-5.

Di Tommaso et al. "Structure of genipin in solution: a comined experimental and theoretical study" RSC Advances, Jun. 2013, vol. 3, issue 33, pp. 13764-13771. doi:10.1039/C3RA42147C.

Sung et al. "Feasibility study of a natural crosslinking reagent for biological tissue fixation", Journal of Biomedical Materials Research Part A, Dec. 1998, vol. 42, issue 4, pp. 560-567.

Sung et al. "Stability of a biological tissue fixed with a naturally occurring crosslinking agent (genipin)", Journal of Biomedical Materials Research Part A, Mar. 2001, vol. 55, issue 4, pp. 538-546.

Touyama et al. "Studies on the Blue Pigments Produced from Genipin and Methylamine. I. Structures of the Brownish-Red Pigments, Intermediates Leading to the Blue Pigments", Chemical and Pharmaceutical Bulletin, 1994, vol. 42, issue 3, pp. 668-673.

Touyama et al. "Studies on the Blue Pigments Produced from Genipin and Methylamine. II. On the Formation Mechanisms of Brownish-Red Intermediates Leading to the Blue Pigment Formation", Aug. 1994, vol. 42, issue 8, pp. 1571-1578.

"Meat marking inks", https://web.archive.org/web/20150309095631/http://www.idandtrace.com/meatmarkingink.htm, Mar. 9, 2015 (Mar. 9, 2015).

"Lee et al., ""Colorimetric determination of amino acids using genipin from Gardenia jasminoides"", Anal. Chim. Acta., 480, 267-274, 2003".

Slusarewicz et al., "Kinetic analysis of genipin degradation in aqueous solution.", Nat. Prod. Commun., 5, 1853-1858, 2010.

* cited by examiner

BODY INK COMPOSITIONS AND APPLICATORS

TECHNICAL FIELD

The invention relates to the field of body and tattoo inks, and specifically to a temporary body ink composition and an applicator therefor.

BACKGROUND

Temporary tattoo or body inks are well known in the art, and have been used to decorate the human body for various purposes throughout human history. Body decoration is widespread through much of the world. The use of temporary inks or other substances to temporarily decorate the body is also widespread, ranging from henna tattoos to synthetic inks designed to have a temporary effect. Various methods and compositions for applying the inks result in different lifespans of the tattoo itself.

A number of compositions for providing temporary tattoos or body decorations have been used to generate such inks historically, ranging from ash to clay to colourants from plants. Very little has historically been known about the long term effects of applying many of these compositions to the human body.

Permanent tattoo inks are also widespread, although their application is often painful and the permanent nature of these inks either dissuades people from using them or otherwise leads to self-evident problems with having permanent markings on the human body.

The use of temporary tattoos has gained in popularity in recent years. Parents are more accepting of these for use on their young and pre-adult aged children, and they have become a useful expressive tool for users of all ages for purposes ranging from general artistic or personal expression to showcasing support around pop culture and sporting events.

Many prior art tattoo and body inks suffer from problems related to the length of time the inks are effective being too short and/or being rendered ineffective too easily through regular wear activities. In addition, the health side effects of some of the elements used in prior art permanent and temporary tattoo inks have either not been extensively studied or have been shown to have at least some detrimental effects. Accordingly, there is a need in the art for an improved temporary tattoo/body ink.

SUMMARY OF THE INVENTION

In a first embodiment of the invention, there is disclosed a temporary tattooing ink comprising a concentrated genipin solution including a solvent and dissolved genipin; wherein the amount of dissolved genipin is in the range of 10 mM to 500 mM and wherein the dissolved genipin has a purity of at least 85%.

In one aspect of the first embodiment, the solvent is selected from pure water and buffered water.

In another aspect of the first embodiment, the solution has a pH of 7.4+/−2.0.

In another aspect of the first embodiment, the solution has a pH of 7.4.

In another aspect of the first embodiment, the buffer is phosphate buffered saline.

In another aspect of the first embodiment, the solution further includes an organic co-solvent, such as ethyl acetate, acetone, dimethyl sulphoxide, dimethylformamide, tetrahydrofuran, diethyl ether or most preferably isopropyl alcohol or ethyl alcohol.

In a second embodiment of the invention, there is disclosed a temporary tattooing ink comprising genipin, a solvent and a thickening agent.

In one aspect of the second embodiment, the temporary tattooing ink further comprising isopropyl alcohol, or an organic co-solvent including, but not limited to, ethyl acetate, acetone, dimethyl sulphoxide, dimethylformamide, tetrahydrofuran, diethyl ether.

In another aspect of the second embodiment, the thickening agent is xanthan gum.

In another aspect of the second embodiment, the ink further includes a vegetable oil.

In another aspect of the second embodiment, the ink includes an oil selected from the group consisting of oils from canola, rosemary, olive, coconut, corn, cottonseed, palm, peanut, safflower, sesame, soybean, sunflower, almond, cashew, hazelnut, macadamia, pecan, pistachio, walnut and acai.

In another aspect of the second embodiment, the ink includes glycerol.

In another aspect of the second embodiment, the thickening agent is selected from the group consisting of natural gums and polysaccharides.

In another aspect of the second embodiment, the solvent is water and the ink contains 75 to 99 percent by volume water and 1-25 percent by volume vegetable oil, and 1-20% organic co-solvent.

In another aspect of the second embodiment, the xanthan gum is provided at a mass fraction of between 0.1-0.15.

According to a third embodiment of the invention, there is disclosed an applicator for applying a temporary tattooing ink comprising a multi-layered pad having a first adhesive layer, a second adhesive layer, an ink-containing layer and a cut-away top layer; wherein a tattoo design is cut into each of the first and second adhesive layers and a temporary tattooing ink is absorbed into the ink containing layer; the temporary tattooing ink comprising genipin.

In one aspect of the third embodiment, each of the first and second adhesive layers are double-sided adhesive layers.

In another aspect of the third embodiment, the ink-containing layer is formed from a non-woven material into which the genipin is embedded.

According to a fourth embodiment of the invention, there is disclosed a method for applying a temporary tattoo ink to the applicator as described above comprising embedding the genipin into the non-woven material by either dipping the ink-containing layer into an aqueous solution of genipin prior to assembling the multi-layered pad or pipetting the genipin onto the assembled applicator.

In one aspect of the fourth embodiment, the genipin forms part of a solution and is warmed to approximately 40 degrees Celsius prior to being embedded into the non-woven material.

DETAILED DESCRIPTION

Fruit juices extracted from genipin-containing fruits, such as *Genipa Americana*, have been used in tattoo and body ink compositions in the prior art. The extracted fruit juice includes residual amine-containing groups which react with the genipin forming a bluish color. Some of this reacted genipin complex is unable to then react with collagen and other anchored amine-containing groups found on human skin, leading to the waste of a portion of the extracted genipin. In addition, the genipin progressively reacts with the amine groups found in the juice, thus leading to an expiration date of the ink composition, unless it is frozen. Furthermore, the juice may contain residual sugars and other compounds that may attract contamination (e.g. bacterial contamination) or which are not beneficial or may hinder the tattooing process.

The improvement of the invention includes, inter alia, a concentrated genipin solution. The concentrated genipin improves the overall kinetic reaction allowing the staining and inking to proceed significantly faster than prior art inks. In addition, the concentrated genipin solution results in there being a controlled amount of amine functional groups, allowing colouration of the solution while keeping >95% of the genipin for art inks. Accordingly, the shelf-life or expiration date of the composition of the invention is extended by orders of magnitude over the prior art use of genipin juices. Experiments have shown that the composition of the invention has a shelf-life of several years, whereas prior art genipin fruit juice extracts have a shelf-life of several weeks.

The concentrated genipin is typically obtained in solid form and can readily be obtained having a purity of greater than 98%. The invention is not limited by this level of purity although it is preferred that a purity greater than 85% be employed to benefit from the advantages as herein described.

It is contemplated that the composition may be provided in a number of forms, although it is preferred to either be provided in a liquid form or in a gel form. The liquid form of the composition would typically be used with an applicator, such as a non-woven material, whereby the applicator is soaked or otherwise dipped in the liquid form to be later applied to the human skin by the application of pressure onto the applicator. In the gel form, the composition may be applied directly to the skin. Further details on these application methods will be discussed below.

Formula 1—Liquid Form

In liquid form, the composition consists of at least a solvent and dissolved genipin in an amount in the range of 10 mM to 200 mM (millimolar), with a preference towards the upper end of this range. The 10 mM value is the minimum concentration required for staining to take effect, whereas 95 mM is the solubility limit of the composition. The ultimate upper limit of 200 mM is the amount where the tattoo applicator becomes too stiff and ultimately impractical to use. The solvent may be pure water, or alternatively buffered water. It has been discovered that maintaining an optimal pH of 7.4 produces the highest degree of effectiveness. Use of a buffer allows such a pH to be accurately maintained at the optimal level of 7.4. However, for efficacy pure water may be used instead of buffered water. The pH of water is 7.0, which reasonably approximates the determined optimal pH, and is within a range of pH values which lead to preferred results. In a preferred embodiment, isopropyl alcohol or ethyl alcohol is added to the formulation to provide enhanced drying capabilities and increased genipin solubility.

Generally, the use of water as the solvent is preferred over other possible solvents because certain steps in the inking or staining reaction depend on water as a catalyst. In particular, the first attachment of genipin to an amine-containing group in the human skin, to the chemical and structural reconfiguration of the molecule leading to colour change depends on water as the catalyst. Since the overall reaction kinetics depends also on diffusion, it is also preferred to use a solvent with low viscosity. It is well known that diffusion levels decrease as the viscosity of a liquid increases. Water has a viscosity of 1 centipoise (cP), which is a very low level and one that has been determined to be preferred for the composition of the invention. In addition to the low viscosity advantages, the catalytic nature of water is especially beneficial—in particular, the combination of the low viscosity and catalytic nature make water-based solutions optimal. Other solvents tested include viscous solutions such as syrups mixed with different amounts of water resulting in a viscosity in the range of 500-3500 cP, in addition to glycerol mixed with water and syrup-glycerol-water combinations in that same viscosity range.

In embodiments where a buffer is used with water, the preferred buffer is phosphate buffered saline (PBS) having a pH of 7.4. Other buffers are also contemplated, and the invention is not to be considered limited to the use of PBS. The definition of a buffer solution is "an aqueous solution consisting of a mixture of a weak acid and its conjugate base, or vice versa." The buffering solution should be primarily water (on a weight/volume basis). The weak acid or conjugate base should yield a buffering solution with a useful pH range around 7.4+/−2.0. The error bar is applied to incorporate a wide range of buffers.

When mixing the genipin composition, the solid genipin may be added completely to the solvent and left to dissolve. Alternatively, and in order to speed up the dissolution of the genipin, the solution may be heated, provided the temperature is kept below 121° C., which is the melting point of genipin. Vigorous mixing or stirring may also be used to speed up dissolution.

In use, the liquid composition of the invention is preferably soaked in a fabric pad, most preferably a non-woven material, which is then attached to a stencil outlining the design of the tattoo being applied and pressed onto the skin. The absorbent pads may be presoaked or soaked just prior to use with a water wetted cloth. When presoaked, the total absorbency is most preferably between 0.5 mL and 7.5 mL depending on the size of the stencil. The swelling capacity of the fabric should be approximately 45% to ensure an accurate tattoo is generated, with minimal run-off. The fabric is preferably made from a water absorbing material, generally of a cellulosic of fibre base which is capable of holding water content up to 15 times is weight. Cotton pads are common and meet this requirement.

Formula 2—Gel Form

In a preferred embodiment of the invention, the composition is provided in a gel form, which can be applied directly to the body or with the aid of an applicator to assist in generating the appropriate design. The gel form does not require absorption into a fabric pad as the liquid form would.

The preferred embodiment of the gel form consists of vegetable oil, water, xanthan gum, ethyl or isopropyl alcohol and genipin. The vegetable oil may be substituted or supplemented by any natural or essential oil, including but not limited to oils from canola, rosemary, olive, coconut, corn, cottonseed, palm, peanut, safflower, sesame, soybean, sunflower, almond, casher, hazelnut, macadamia, pecan, pistachio, walnut, acai and others. In other embodiments, glycerol is used in place of vegetable oil or long chain fatty acids. Generally, alternatives to the vegetable oil are non-toxic, organic, non-amine-containing liquid compounds. The alcohol may be substituted or supplemented by any other organic solvent, including but not limited to butyl alcohol, acetone, ethyl acetate, dimethyl sulfoxide, dimethylformamide, dodecanol and others.

Xanthan gum is used as a thickening agent, which absorbs water and increases the viscosity of the gel without substantially changing its other properties. Various other thickening agents may be used, including natural gums such as alginin, locust bean, guar, acacia, oat, karaya, tara, gellan, ghatti, konjac, cassia, tragacanth, arabinogalactan, carob, spruce, chicle, dammar and curdlan. Other polysaccharides that may be used as thickeners include pectin, carrageenan, pullulan, baker's yeast glycan, and soybean hemicellulose.

The genipin concentration range is the same as for formula 1 above: 10 mM to 500 mM. The water, vegetable oil, a co-organic solvent and xanthan gum may be added at different concentrations, as exemplified in Table 1:

|  | Approx. Volume (mL) | Approx. Mass (g) | Volume fraction range | Mass fraction range |
| --- | --- | --- | --- | --- |
| Water | 20.55 | N/A | 0.75-0.99 | N/A |
| Vegetable oil | 5.45 | N/A | .01-.25 | N/A |
| Xanthan gum | N/A | 1.35 |  | 0.01-0.15 |
| Organic Solvent | 5 | N/A | .01-.25 |  |

In Table 1, the volume fraction and mass fraction ranges shown are intended to illustrate alternative compositions of water, vegetable oil, xanthan gum and organic solvent. For example, for a total volume of 25 mL, the volume of water may range from 18.75 mL to 24.75 mL. Similarly, the total volume of vegetable oil may range from 0.25 mL to 6.25 mL. For a total mass of 25 g, the mass of xanthan gum may range from 0.25 g to 3.75 g. Finally, the totally amount of the co-organic solvent would be approximately 5 mL or 0.01-0.25 volume fraction in general.

An alcohol, such as isopropyl alcohol or ethyl alcohol is added to the gel to enhance skin absorption and dying capabilities. The preferred amount of isopropyl alcohol/ethyl alcohol added is in the range of 5-40% by volume. The alcohol is added upon dissolution of the genipin in water.

In preparing the preferred embodiment of the gel, the first step is the addition of xanthan gum to the desired oil. If xanthan gum is added directly to the solvent, it clumps together and becomes difficult to distribute thoroughly, requiring undesired vigorous mixing for an extended period. This mixing introduces bubbles into the solution, which decreases the quality of the tattoo that can be prepared. Xanthan gum is a carbon based compound, which is mildly hydrophobic. Therefore, it dissolves better in organic compounds like vegetable oil.

The water/genipin mixture is prepared separately. The water/genipin mixture is added directly to the xanthan gum/vegetable oil mixture. The two are then stirred or otherwise mixed. The xanthan gum promotes higher miscibility between the oil and aqueous phase, allowing the two phases to mix completely. The xanthan gum effectively acts as both a thickening agent and an emulsifier. It is beneficial to decant any excess oil that rises to the top and does not fully mix. The resultant gel is then ready and may be stored in plastic bottles.

The invention as herein described provides for an improved tattoo and body ink composition, which has a temporary effect on the body. In various experiments, and depending on the specific constituent elements and application method used, the temporary tattoo will typically last from between 10-18 days at consistency of coloration, whereas the entire tattoo is uniform in its appearance without noticeable cracking or deterioration in quality. The ink generally fades over time and leaves no lasting effects on the human body. The ink itself is relatively easy to apply to the body and various designs may be used by way of a stencil.

Formula 3—Preferred Application

In another variation of the invention, which includes a preferred method and device for applying the temporary tattoo to the body, the active ingredient (genipin) is embedded into an applicator with a stencil etched into the bottom, either via a dye-cutting or laser cutting process.

Figure 1:
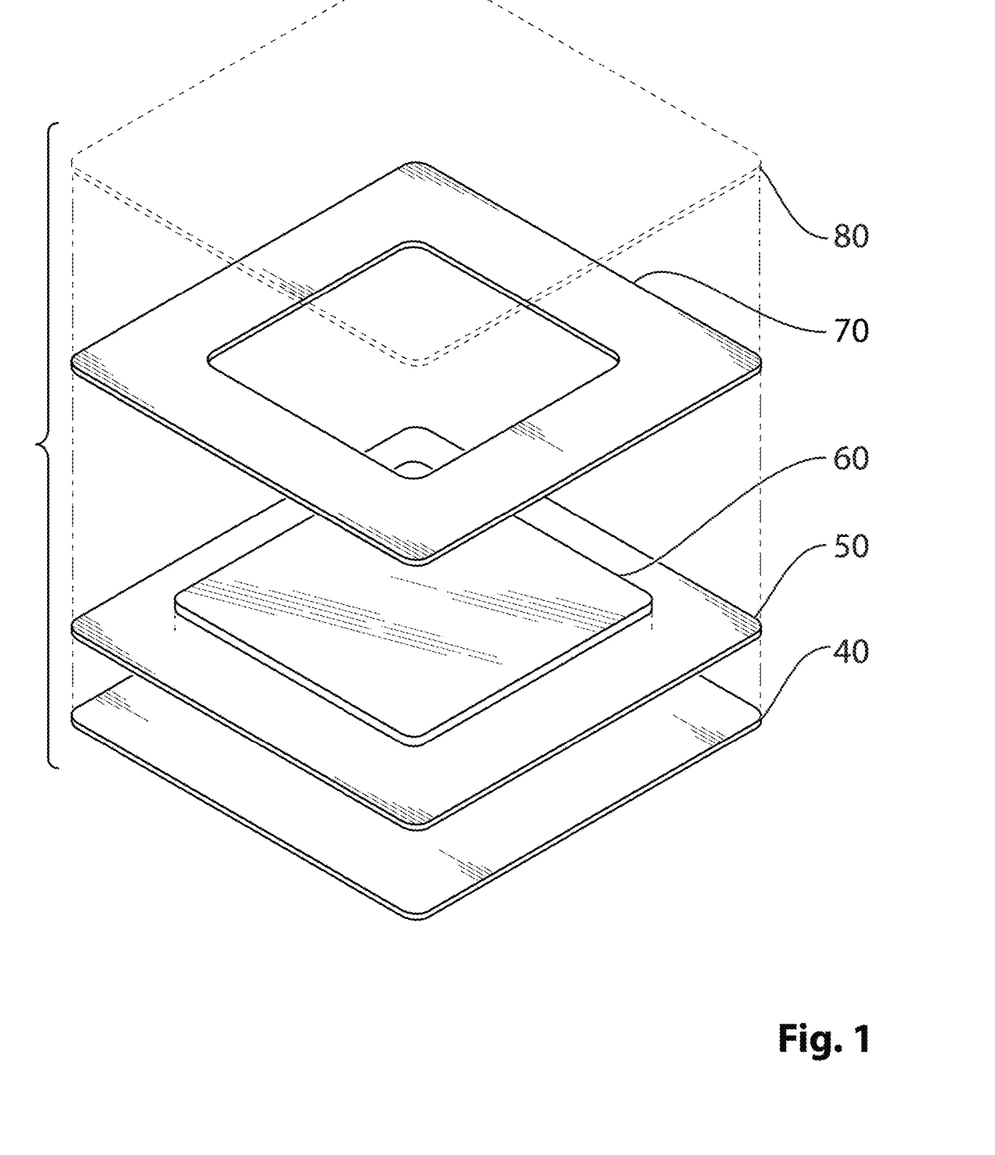
FIG. 1 shows an exemplary applicator for applying the temporary tattoo as herein described.

Referring to FIG. 1, there is shown a preferred embodiment of the invention in which an applicator 5 includes four layers. The bottom layer 40 is a double-sided medical adhesive, such as that sold by 3M™ as medical adhesive 9835. Above this layer is a secondary adhesive 50, preferably medical grade such as that sold by 3M™ as medical adhesive 1509 or CCT MD-1320. The intended temporary tattoo design (not shown) is cut into each of these layers. Above the secondary adhesive is a non-woven material 60, such as that sold as Delstar™ Stratex in which the active tattooing ingredient, ie. the genipin as herein described, is embedded. Finally, a top layer 70 is one which is cut in a way that the centre is exposed to unveil the non-woven material 60. The layer 70 could be 3M 764 or Mactac™ VDG 9511.

The genipin may be added to the non-woven material using various methods. In one exemplary method, the pre-cut non-woven material is dipped into an aqueous solution of genipin, typically in the 75 mmol-200 mmol range, or by pipetting the same concentration solution onto the non-woven material in the fully assembled applicator 5. Genipin has limited solubility in water, therefore the solution is warmed to approximately 40 degrees Celsius in order to bring it into solution. Alcohol can be added to the aqueous solution in order to increase genipin solubility. If pipetting, the optimal volume required is in the range of 0.8 mL per square inch of the non-woven material. These are allowed to dry for approximately 24 hours and a protective layer 80 is optionally added to prevent the genipin from staining a user's hands.

Figure 6:
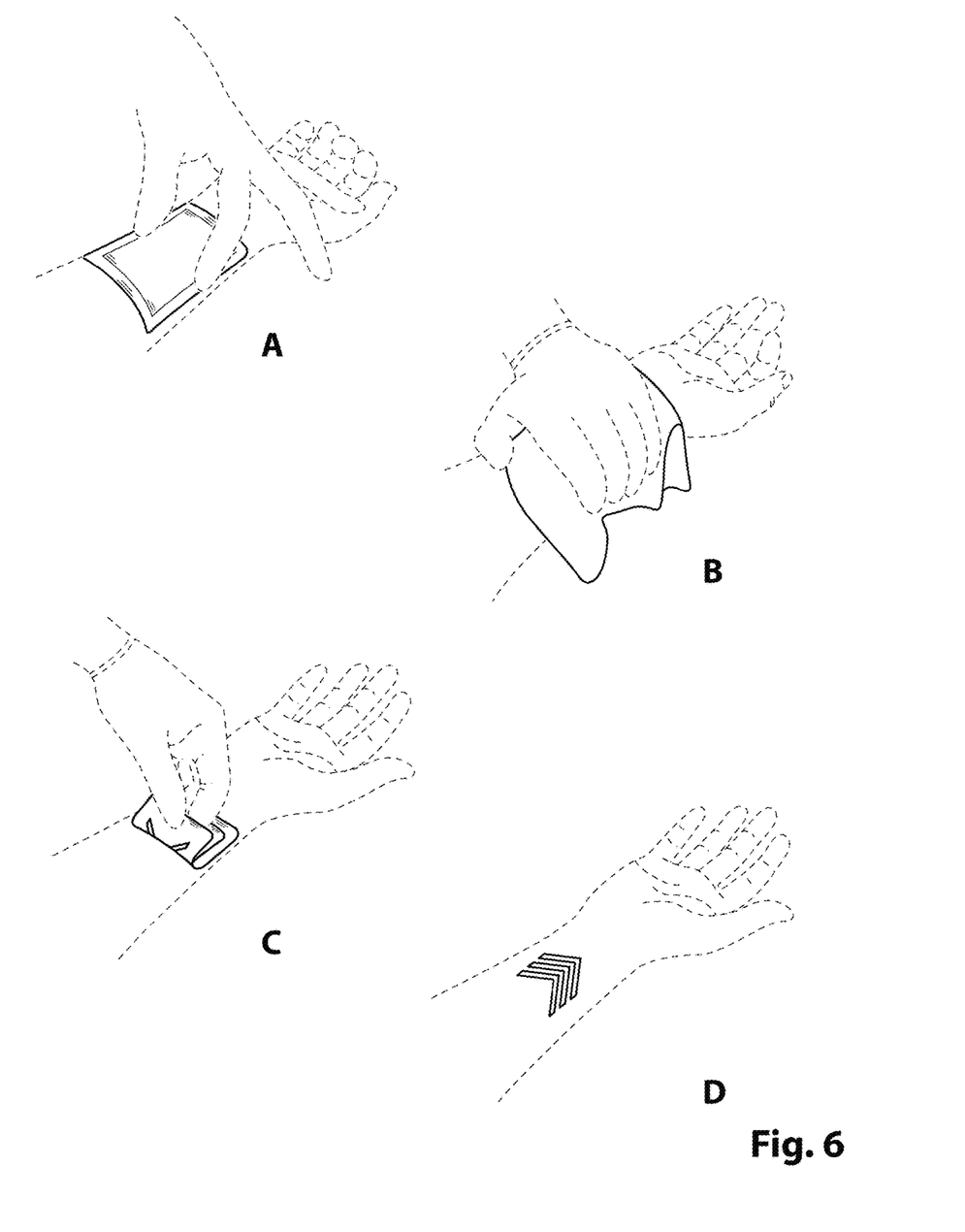
FIG. 6 shows an exemplary method of applying a temporary tattoo to a user's skin.

Referring now to FIG. 6, from a user's perspective, in order to apply the temporary tattoo using the applicator 5, the bottom layer 40 is first peeled off, revealing the sticky side of the secondary adhesive 50. The sticky side is then applied to the skin and pressure applied by manually pressing down. The top layer 80 is then peeled off to expose the activated non-woven material 60. With the non-woven material 60 pressed onto the skin (A), an alcohol swab (such as ethanol or isopropanol) is wiped over the non-woven material by rubbing; and a moistened towel is heated (such as by microwaving for 15 seconds) and pressed firmly over the tattoo applicator 5 (B). The water level of the moistened towel is ideally approximately 1.5 oz of water per 9×9" towel. After approximately 5-15 minutes, the towel and applicator are removed (C) and can be discarded, yielding the temporary tattoo (D) which darkens over the next 36 hours to maximum intensity.

In order to more thoroughly explain the operating principles behind the invention, a detailed review of various literature and experimentation was carried out. These are now presented below.

Principles of Operation

A list of references is provided at the end of this description to which the references in the following paragraphs refer.

Finnegan et al. (1960) isolated from the ripe fruit of *Genipa americana* L. (binomial name), its "active" principle—the part of the plant responsible for its dyeing properties—as a crystalline colourless solid, which has been named genipin.[1] Genipin corresponds to the molecular formula $C_{11}H_{14}O_5$. Over the past several decades, the exact structure of genipin has been studied and precisely determined. Furthermore, researchers have been investigating the exact mechanism of reaction that produces the dark-blue pigment, in addition to the molecule's cross-linking properties for bioprostheses. The latter is particularly of interest due to genipin's high biodegradability and low cytotoxicity (harmfulness to cells).

Genipin, an iridoid (metabolite), is primarily produced from the enzymatic hydrolysis of geniposide, found in the fruit of *Genipa americana*, as well as Gardenia jasminoides and several other plants, although other synthetic production mechanisms have been developed. These plants are well known as a source of colourants used in food chemistry. Aimed at designing new and low-impact chemical systems, great efforts have been made to mimic natural structures and functions. Naturally coloured/chromophore-containing molecules such as genipin are increasingly studied to develop new technologies and obtain nontoxic and effective final products[2,3]. For example, Di Tommasso et al. (2014), funded in part by L'Oreal Research and Innovation, present a mechanistic theoretical study on genipin reactivity.[4]

Despite the industrial interest of genipin and its wide range of possible applications, its full characterization and reactivity are far from being cleared up. For instance, the structure of genipin in solid state has just recently been characterized. Some hints are also available in literature about the behavior of genipin in solution. In particular, it has been noted that, at basic pH, genipin is unstable and undergoes self-polymerization, whereas in milder pH conditions[5], a ring-opening reaction has been proposed.[6,7]

Nonetheless, it is well known in the field of colouring research that the reaction between genipin and amine groups yields blue pigments.[8,9] This occurs through either primary amines or amino acids, which are present in proteins—and human skin. It was reported by Touyama et al. that only primary amines, rather than secondary or tertiary amines, can react with genipin.[6] This claim is confirmed by Sung et al. (1998) in a feasibility study of genipin as a natural cross-linking agent for biological tissue fixation.[10]

Figure 2:
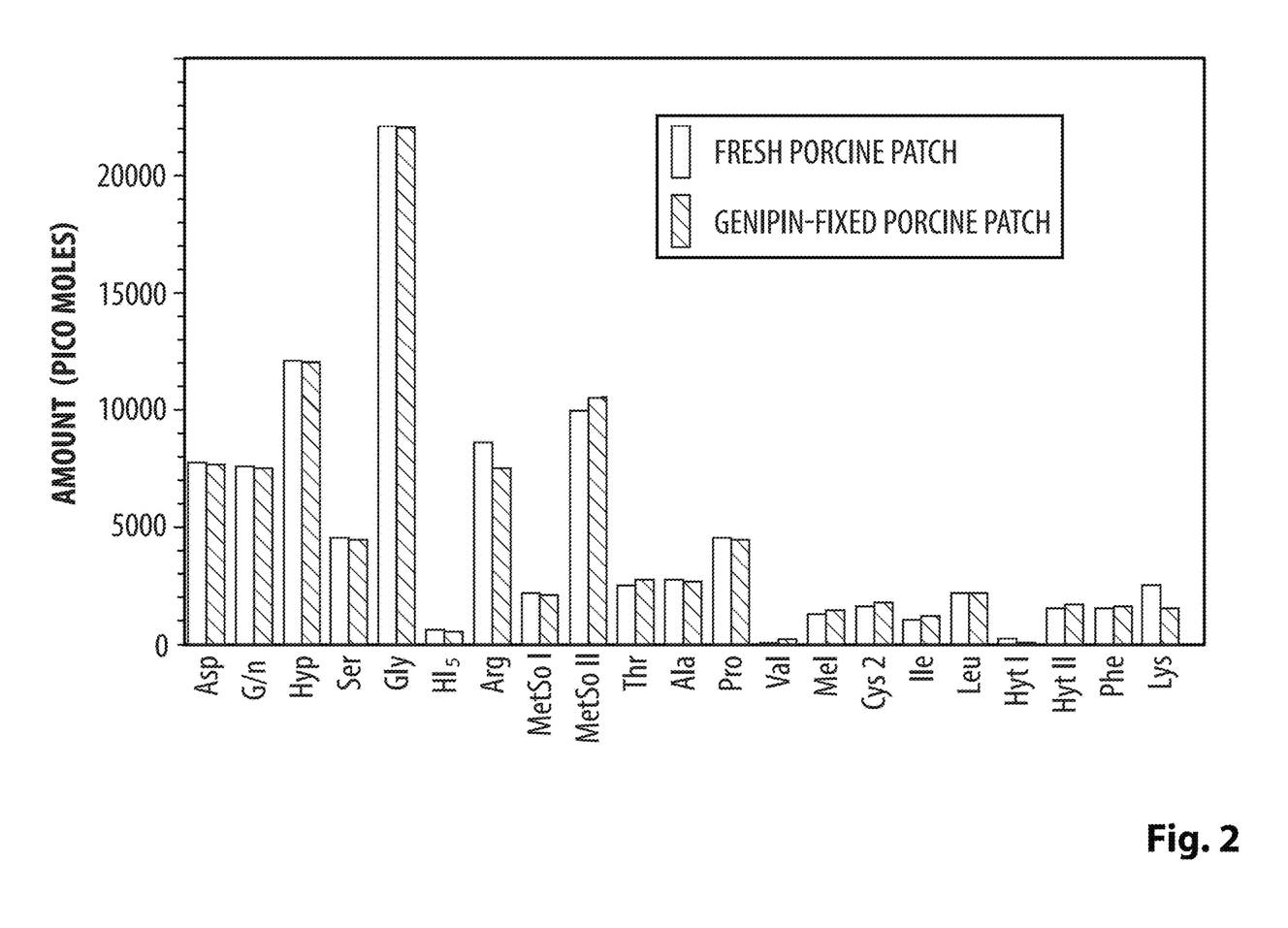
FIG. 2 charts the amounts of each amino acid residue present in the fresh and genipin-fixed porcine pericardia obtained in an amino acid analysis.

Sung et al. use fresh porcine pericardia procured from a slaughterhouse in order to mimic human skin and determine the cross-linking and dyeing properties of genipin. After fixation, it was found that the biological tissue fixed with genipin became dark bluish.[11] They determined that the amino acid residues that may react with genipin are lysine, hydroxylysine, and arginine, as demonstrated in FIG. 2. Of these reacted amino acid residues, lysine was the most reactive. These all have primary amino groups. Note: Later researchers have identified other amino acids that may react.

Figure 3:
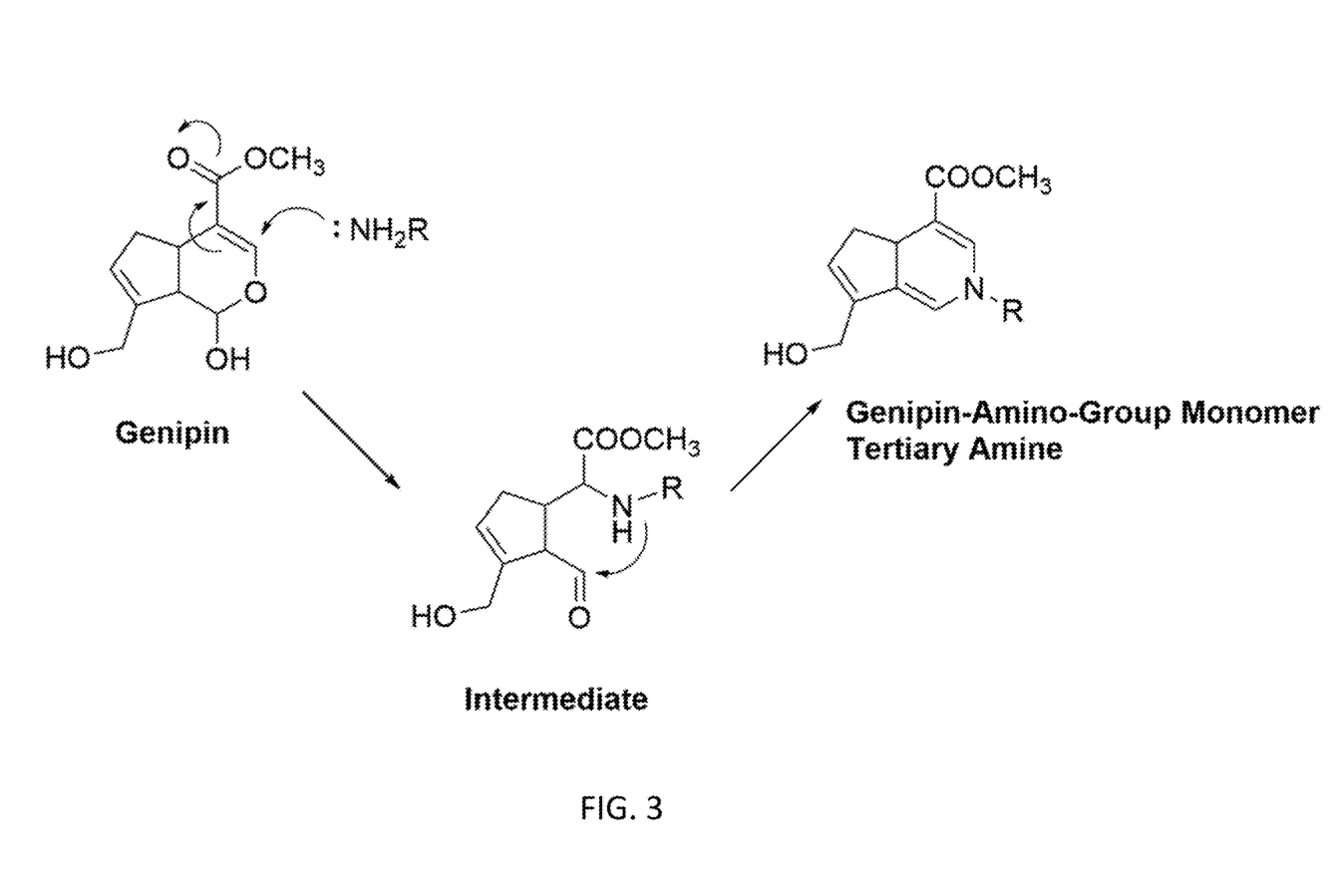
FIG. 3 shows a proposed simplified mechanism of blue-pigment formation.

Touyama et al. (1994) studied the structures of the intermediates leading to a blue pigment produced from genipin and methylamine, the simplest primary amine. The genipin-methylamine monomer and the blue pigment polymers proposed by Touyama's group may be found in the literature.[12,13] Briefly, the genipin-methylamine monomer is formed though a nucleophilic attack by methylamine on the olefinic carbon at C-3 of genipin, followed by opening of the dihydropyran ring and attacked by the secondary amino group on the resulting aldehyde group (shown in FIG. 3). The blue-pigment polymers are presumably formed through oxygen radical-induced polymerization and dehydrogenation of several intermediary pigments.

Similar results explaining the reaction mechanism were also reported by Fujikawa et al.[12,13] In the study of the structure of a blue pigment formed from glycine (another amino acid) and genipin, Fujikawa's group found multiple blue components. They reported that the simplest component in the blue pigment was a 1:1 adduct (direct addition of molecules). From the structure of this simplest component, they proposed that genipin reacts spontaneously with an amino acid to form a nitrogen-genipin complex, which undergoes dehydration to form an aromatic, stable monomer. Dimerization occurs at the second stage, perhaps by radical reaction.

Figure 4:
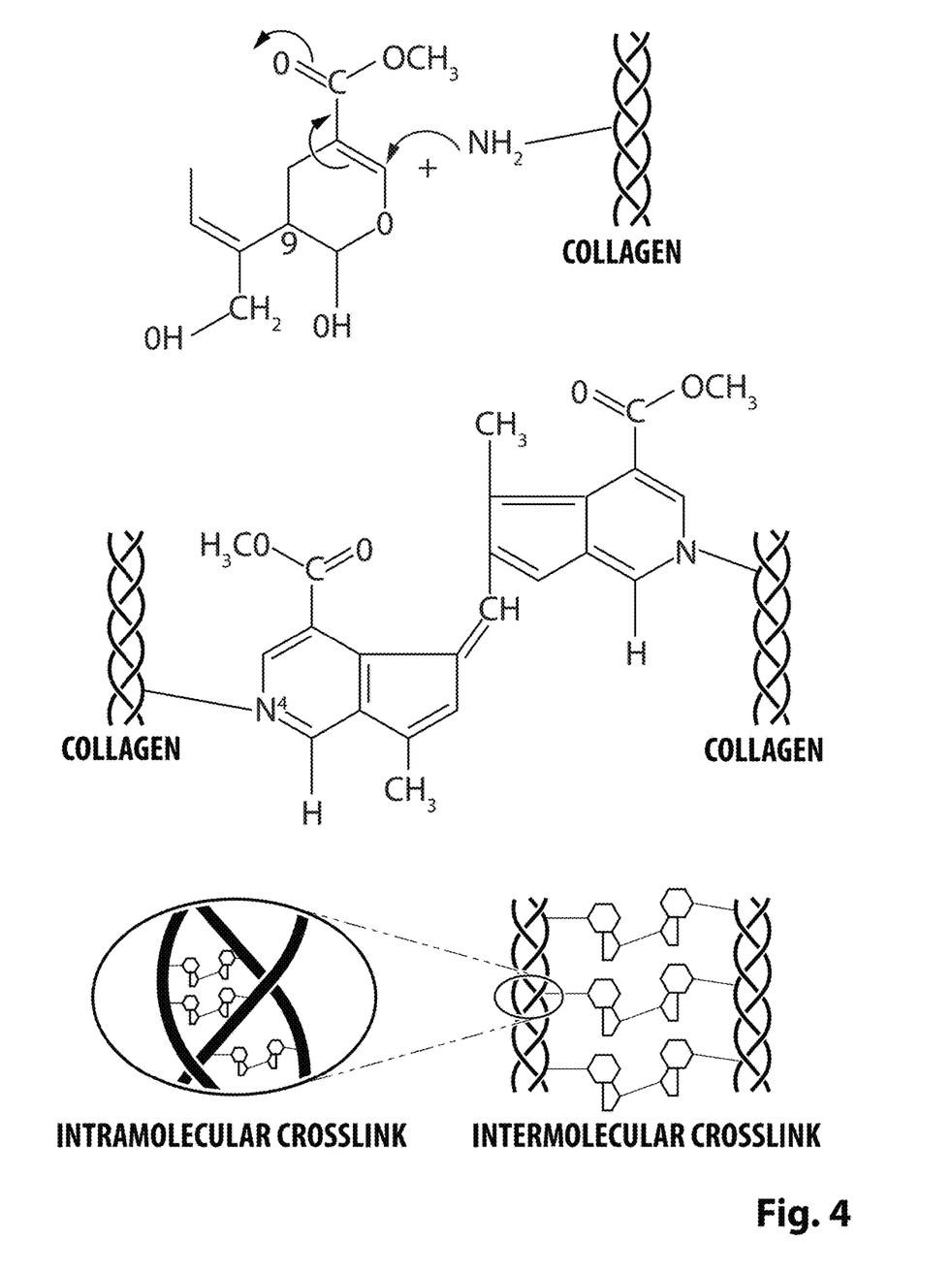
FIG. 4 shows a genipin-collagen reaction.

The results of the aforementioned studies suggest that genipin may form intra-molecular and intermolecular cross-links with cyclic structure within collagen fibers in biological tissue (shown in FIG. 4).

A drastic colour change of the solution, from colourless to yellow to red, was observed with reaction progress. These experimental investigations allowed for the identification of two species, namely a yellow intermediate, and the fully characterized product, 2-methyl-4-methoxycarbonyl-8-methyl-2-pyridine. The latter gives a reddish colour to the solution and is supposed to be the starting point for the production of blue oligomers.

Figure 5:
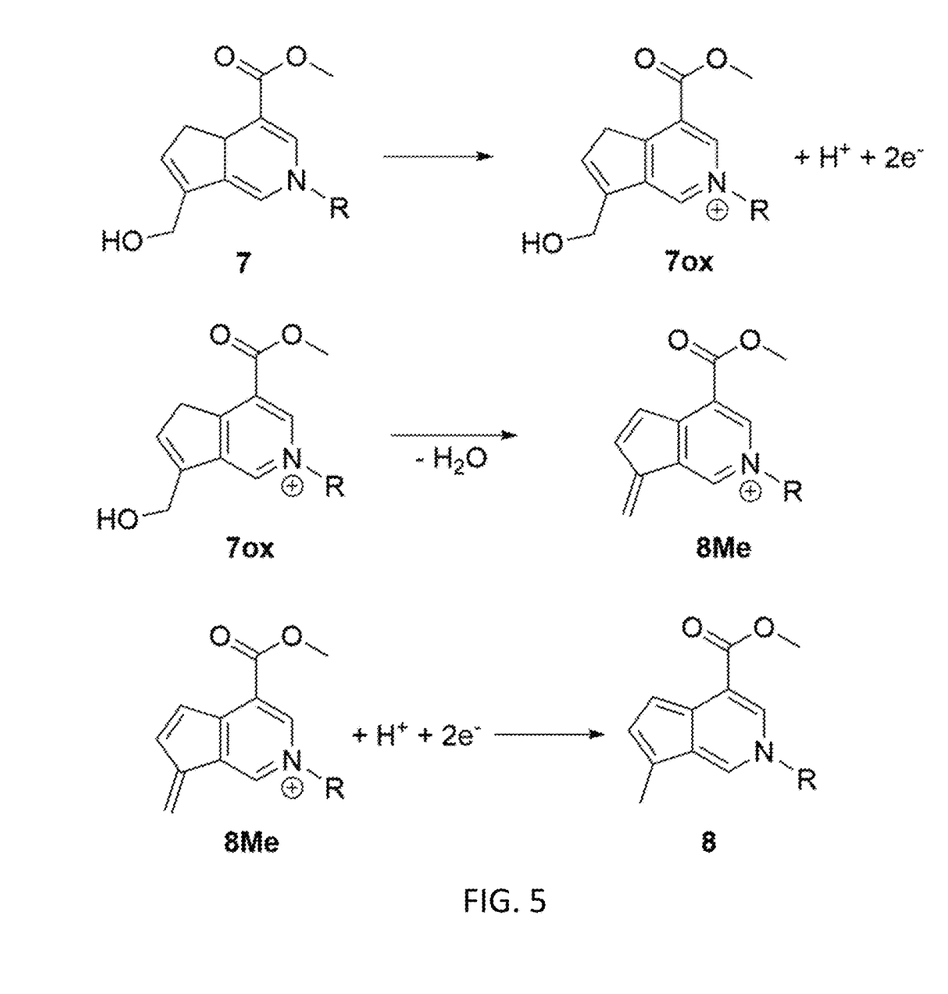
FIG. 5 shows a partial reaction mechanism towards blue pigment

According to Di Tommasso et al., who performed an extensive experimental investigation to determine the step-by-step reaction mechanism, from a thermodynamic point of view, the activation barriers for all the reactions is low, and the endothermicity (absorption of heat) is not dramatic, and so the reaction proceeds mainly self-catalytically and without stop towards the final blue product. A partial representation of the complex reaction mechanism is shown in FIG. 5.

It should also be noted that the first oxidation of 7 has not been unequivocally determined and the presence of an oxidant (such as oxygen) is probably necessary to trigger the cycle. The catalytic role of water has been highlighted in many steps of the process, until the production of the first yellow intermediate 4.

In a 1986 patent, researchers from Suntory Limited demonstrate that the reaction of genipin with taurine, a type of aminosulfonic acid, results in a blue dye composition with far better stability than the known gardenia (similar to *americana*) derived dyes. Furthermore, it is shown that varying the pH in the range of 4-9 changes the dye colour from dark blue to bluish purple 14. This is consistent with the study produced by Di Tommasso et al., and it is clear in FIG. 5 that the pH may alter the equilibrium between components.

Existing Methods to Alter *Genipa's* Dyeing Properties

In the Wild Flavors, Inc. patent, there is described a method of manufacturing a red colourant by using a genipin-rich extract. First, the genipin extract is hydrolyzed to remove a methyl group and convert the genipin to genipinic acid. Then the hydrolyzed genipin is neutralized using acids, and then heated to 70-75° C. for 10-20 minutes. The solution is then purified by filtration or centrifugation methods to remove an insoluble brown product. Finally, the solution is adjusted to a pH of 4.0-4.6 with organic acid or salt, such as acetic acid or sodium acetate. Red colour is generated after mixing with amine-containing compounds and heating to about 70-95° C. for about 2 hours—not feasible for use as a tattoo. The *genipa* red is a heat-stable pigment, and is also stable at a high pH.[15]

In Ecoflora S.A.S. patent, there is described colourant compounds and methods of isolation of the colourant compounds derived from a reaction with genipin and an amine. In the introduction of the patent, the inventors describe the results of an exhaustive patent search and literature analysis aimed at finding all existing solutions to change the dyeing colours of genipin and genipin analogs derived from *Genipa americana*. These solutions have been described above. Furthermore, the authors assert that "the present invention contributes to overcome the lack of knowledge regarding the molecular structures of the blue pigment material derived from a reaction of genipin with an amino acid.[16] This statement is supported by the experimental results of Di Tommasso et al.

The authors provide methods of preparing purple, black, and green colourants from the juice of *Genipa americana*. The juice extract is reacted with either glycine, proline or tryptophan (types of amino acids), followed by isolation steps.[16] It is unclear whether this formulation would dye human skin, and would depend on whether the cross-linking properties of genipin are maintained.

REFERENCES

1. Finnegan, R. A., G. *Naturally Occurring Oxygen Heterocyclics*. Journal of Organic Chemistry. (1960) 110(9), 2174-2177.
2. D. Frick, Rev. Prog. Color. Relat. Top. (2003) 33, 15.
3. O. J. X. Morel and R. M. Christie. *Current trends in the chemistry of permanent hair dyeing*. Chem. Rev. (2011) 111, 2537.
4. Di Tommaso, S., David, H., Gomar, J., Leroy, F., & Adamo, C. *From iridoids to dyes: a theoretical study on genipin reactivity*. RSC Advances, (2014) 4(22), 11029.
5. F. L. Mi, S. S. Shyu and C. K. Peng, J. *Characterization of ring-opening polymerization of genipin and pH-dependent cross-linking reactions between chitosan and genipin*. Polym. Sci., Part A: Polym. Chem. (2005) 43, 1985.
6. J.-E. Park, J.-Y. Lee, H.-G. Kim, T.-R. Hahn and Y.-S. Paik, J. Agric. *Isolation and characterization of water-soluble intermediates of blue pigments transformed from geniposide of Gardenia jasminoides*. Food Chem. (2002) 50, 6511.
7. P. Slusarewicz, K. Zhu and T. Hedman. *Kinetic analysis of genipin degradation in aqueous solution*. Nat. Prod. Commun. (2010) 5, 1853.
8. S. W. Lee, J.-M. Lim, S.-H. Bhoo, Y.-S. Paik and T.-R. Hahn Structure of genipin in solution: a combined experimental and theoretical study. Anal. Chim. Acta. (2003) 480, 267.
9. S. Fujikawa, *Brilliant skyblue pigment formation from Gardenia fruits*. Tetrahedron Lett. (1987) 28, 4699. 11
10. Sung, H., Huang, R., Huang, L. L. H., Tsai, C., & Chiu, C. *Feasibility study of a natural crosslinking reagent for biological tissue fixation*. (1998).
11. Sung, H., Liang, I., Chen, C., Huang, R., & Liang, H. *Stability of a biological tissue fixed with a naturally occurring crosslinking agent (genipin)*. (2000).
12. Touyama R, Takeda Y, Inoue K, Kawamura I, Yatsuzuka M, Ikumoto T, Shingu T, Yokoi T, Inouye H. *Studies on the blue pigments produced from genipin and methylamine. I. Struc-tures of the brownish-red pigments, intermediates leading to the blue pigments*. Chem Pharm Bull. (1994). 42:668-673.
13. Touyama R, Inoue K, Takeda Y, Yatsuzuka M, Ikumoto T, Moritome N, Shingu T, Yokoi T, Inouye H. *Studies on the blue pigments produced from genipin and methylamine. II. On the formation mechanisms of brownish-red intermediates leading to the blue pigment formation*. Chem Pharm Bull. (1994) 42:1571-1578.
14. Koga, K., Fujikawa S., Fukui, Y. *Natural blue dye composition and colorant using the same: prepared by reacting taurine and genipin*. (1988) EP0251063 A2.
15. Wu, S., and Horn, G. *Genipin-rich material and its use*. (2013) US2012/063836.
16. Varas, E., et al. *Colorant compounds derived from genipin or genipin containing materials*. (2014) US patent application 2014/0350127.

The invention claimed is:

1. A temporary tattooing ink comprising a concentrated genipin solution comprising water or buffered water and dissolved genipin; wherein the amount of dissolved genipin is in the range of 10 mM to 500 mM and wherein the dissolved genipin has a purity of at least 85%; wherein the solution has a pH of 5.4 to 9.4; and wherein the temporary tattoo ink further comprises:
   vegetable oil; and
   a thickening agent;
   wherein the ink contains 75-99 percent by volume water and 1-2.5 percent volume vegetable oil;
   wherein the temporary tattoo ink is in the form of a gel.

2. The temporary tattooing ink according to claim 1, wherein the solution has a pH of 7.4.

3. The temporary tattooing ink according to claim 1, wherein the buffer is phosphate buffered saline.

4. The temporary tattooing ink according to claim 1, wherein the solution further comprises an organic solvent.

5. The temporary tattooing ink according to claim 1, wherein the thickening agent is xanthan gum.

6. The temporary tattooing ink according to claim 1, further comprising an additional oil selected from the group consisting of oils from: canola, rosemary, olive, coconut, corn, cottonseed, palm, peanut, safflower, sesame, soybean, sunflower, almond, cashew, hazelnut, macadamia, pecan, pistachio, walnut and acai.

7. The temporary tattooing ink according to claim 1, further comprising glycerol.

8. The temporary tattooing ink according to claim 1, wherein the thickening agent is selected from the group consisting of natural gums and polysaccharides.

9. The temporary tattooing ink according to claim 4, wherein approximately 5 percent by volume of the organic solvent is present.

10. The temporary tattooing ink according to claim 9, wherein the thickening agent is xanthan gum, and the xanthan gum is provided at a mass fraction of between 0.1-0.15.

11. The temporary tattooing ink according to claim 4, wherein the organic solvent is ethyl alcohol or isopropyl alcohol.

* * * * *